(12) United States Patent
Vidyasagar et al.

(10) Patent No.: US 11,357,747 B2
(45) Date of Patent: Jun. 14, 2022

(54) AMINO ACID COMPOSITIONS FOR THE AMELIORATION OF SYMPTOMS OF HANGOVER

(71) Applicants: ENTRINSIC, INC., Norwood, MA (US); UNIVERSITY OF FLORIDA RESEARCH FOUNDATION, INCORPORATED, Gainesville, FL (US)

(72) Inventors: Sadasivan Vidyasagar, Gainesville, FL (US); Stephen J. Gatto, Norwood, MA (US); Daniel B. Dennison, Tallahassee, FL (US)

(73) Assignees: ENTRINSIC, INC., Norwood, MA (US); UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 16/987,507

(22) Filed: Aug. 7, 2020

(65) Prior Publication Data

US 2020/0368194 A1 Nov. 26, 2020

Related U.S. Application Data

(63) Continuation of application No. 16/000,792, filed on Jun. 5, 2018, now Pat. No. 10,758,506, which is a continuation of application No. 15/528,990, filed as application No. PCT/US2015/061462 on Nov. 19, 2015, now abandoned.

(60) Provisional application No. 62/138,051, filed on Mar. 25, 2015, provisional application No. 62/083,698, filed on Nov. 24, 2014.

(51) Int. Cl.
| | |
|---|---|
| *A61K 31/198* | (2006.01) |
| *A61K 31/197* | (2006.01) |
| *A61K 31/405* | (2006.01) |
| *A61K 31/00* | (2006.01) |
| *A61P 1/00* | (2006.01) |
| *A61P 1/12* | (2006.01) |
| *A61P 3/12* | (2006.01) |
| *A61P 29/00* | (2006.01) |
| *A61P 31/12* | (2006.01) |
| *A61P 31/18* | (2006.01) |
| *A61P 35/00* | (2006.01) |

(52) U.S. Cl.
CPC .......... *A61K 31/198* (2013.01); *A61K 31/197* (2013.01); *A61K 31/405* (2013.01); *A61P 1/00* (2018.01); *A61P 1/12* (2018.01); *A61P 3/12* (2018.01); *A61P 29/00* (2018.01); *A61P 31/12* (2018.01); *A61P 31/18* (2018.01); *A61P 35/00* (2018.01); *A61K 31/00* (2013.01)

(58) Field of Classification Search
CPC .... A61K 31/00; A61K 31/197; A61K 31/198; A61K 31/405
See application file for complete search history.

*Primary Examiner* — Savitha M Rao
(74) *Attorney, Agent, or Firm* — Greenberg Traurig, LLP

(57) ABSTRACT

The subject invention provides therapeutic compositions, and uses thereof for the treatment or amelioration of symptoms of a disease selected from the group consisting of: Ebola virus infection, HIV infection, ataxia, environmental enteropathy, cancer, hangover, inflammatory disease, and porcine epidemic diarrhea. In preferred embodiments, the composition includes a combination of one or more amino acids selected from the group comprising lysine, aspartic acid, glycine, isoleucine, threonine, tyrosine, valine, tryptophan, asparagine and/or serine.

7 Claims, No Drawings

AMINO ACID COMPOSITIONS FOR THE AMELIORATION OF SYMPTOMS OF HANGOVER

RELATED APPLICATIONS

This application is a continuation of U.S. application Ser. No. 16/000,792, filed Jun. 5, 2018, which is a continuation of U.S. application Ser. No. 15/528,990 filed May 23, 2017, filed as application No. PCT/US2015/061462 on Nov. 19, 2015 which claims priority to Provisional Application 62/083,698 titled MATERIALS AND METHODS FOR THE TREATMENT OF INFLAMMATION, AND ALCOHOL TOXICITY, filed on Nov. 24, 2014, and Provisional Application 62/138,051 titled MATERIALS AND METHODS FOR THE TREATMENT OF EBOLA VIRUS SYMPTOMS, filed on Mar. 25, 2015, all of which are incorporated herein by this reference.

BACKGROUND OF INVENTION

Hangover. Hangover symptoms typically begin when a person's blood alcohol drops significantly and is at or near zero. The symptoms are usually in full effect the morning after a night of heavy drinking. Depending on what and how much was consumed, the symptoms may include: fatigue and weakness, thirst, headaches and muscle aches, nausea, vomiting or stomach pain, poor or decreased sleep, increased sensitivity to light and sound, dizziness or a sense of the room spinning, shakiness, decreased ability to concentrate, mood disturbances, such as depression, anxiety and irritability, and rapid heartbeat.

Symptoms of hangovers can be attributed to a buildup of acetaldehyde in the body. Some common hangover symptoms such as fatigue, stomach irritation and a general sense of illness can be further attributed to glutamine rebound. Consumption of alcohol inhibits glutamine. When the drinker stops drinking, the body produces more glutamine than it needs. Increased glutamine levels stimulate the brain leading to a loss of sleep and in turn leading to the fatigue associated with a hangover. Increased amounts of glutamine may also cause tremors, anxiety, restlessness and increased blood pressure. Alcohol consumption can damage the intestinal epithelial cells. In addition, alcohol increases paracellular permeability (leaky gut).

Because alcohol is absorbed directly through the stomach, the cells that line the organ become irritated. The stomach's irritation may also be a factor in some of the other unpleasant symptoms of a hangover, such as diarrhea and lack of appetite. Additionally, alcohol is a diuretic and one of the consequences of heavy alcohol consumption is dehydration. Cysteine breaks down the hangover-causing toxin acetaldehyde in the liver's easily depleted glutathione. Replenishment of potassium lost to alcohol's diuretic effect is also desirable.

Traditional hangover remedies are often ineffective, and some of them may actually exacerbate the symptoms.

Ebola Symptoms. Ebola hemorrhagic fever (Ebola) is a viral disease caused by Ebola virus. The disease results in nonspecific symptoms early and usually causes internal and external bleeding as the disease progresses. Ebola has a very high mortality rate ranging from about 50% to 100% of humans infected. Early symptoms of Ebola are nonspecific and include fever, headache, weakness, vomiting, diarrhea, stomach discomfort, decreased appetite, and joint and muscle discomfort. As the disease progresses, patients may develop other symptoms and signs such as a rash, eye redness, hiccups, sore throat, cough, chest pain, bleeding both inside and outside the body (for example, mucosal surfaces, eyes), and difficulty breathing and swallowing. Ebola symptoms usually appear from about two to 21 days after exposure. It is unclear why some patients can survive and others die from this disease, but patients who die usually have a poor immune response to the virus.

HIV symptoms. Human Immunodeficiency Virus (HIV) is a virus that attacks the immune system resulting in a variety of infections. HIV can also cause a variety of symptoms and some of these symptoms, like diarrhea, may even occur as a result of treatment. Diarrhea is one of the most common complications of HIV. It ranges in severity from occasional loose stools to ongoing (chronic) cases. Identifying the exact cause of diarrhea in HIV infection can help you get the right treatments for long-term management and better quality of life. HIV itself may be a pathogen that causes diarrhea.

Ataxia Symptoms. Ataxia is a neurological sign consisting of lack of voluntary coordination of muscle movements. Ataxia is a nonspecific clinical manifestation implying dysfunction of the parts of the nervous system that coordinate movement, such as the cerebellum. Several possible causes exist for these patterns of neurological dysfunction. Dystaxia is a mild degree of ataxia.

Villus Height and Crypt Number. Intestinal villi are small projections that protrude from the epithelial lining of the intestinal wall. Each villus is approximately 0.5-1.6 mm in length, and comprises a plurality of microvilli projecting from the enterocytes of its epithelium. Each of these microvilli is much smaller than a single villus. The configuration of the villi increase the internal surface area of the intestinal walls which allows for increased absorption. Increased absorptive area is useful because digested nutrients (including monosaccharide and amino acids) pass into the semipermeable villi through diffusion, which is effective only at short distances. In other words, increased surface area (in contact with the fluid in the lumen) decreases the average distance travelled by nutrient molecules, so effectiveness of diffusion increases. The villi are connected to the blood vessels so the circulating blood then carries these nutrients away. Villus capillaries collect amino acids and simple sugars taken up by the villi into the blood stream. Villus lacteals (lymph capillary) collect absorbed chylomicrons, which are lipoproteins composed of triglycerides, cholesterol and amphipathic proteins, and are taken to the rest of the body through the lymph fluid.

Crypts are tubular imaginations of the epithelium around the villi, lined largely with younger epithelial cells which are involved primarily in secretion. At the base of the crypts are stem cells, which continually divide and provide the source of all the epithelial cells in the crypts and on the villi. Intestinal crypts are found in the epithelia of the small intestine, namely the duodenum, jejunum and ileum.

The height of villi and the depth of crypt are considered as the indicators of intestinal functions. Villus height and crypt depth are direct representations of the intestinal environment and may be used as indicators of intestinal health.

Environmental Enteropathy. Environmental enteropathy is a condition believed to be due to frequent intestinal infections. There are often minimal acute symptoms. The condition usually presents itself with chronic problems with absorbing nutrients which may result in malnutrition in children and presents with diarrhea. Environmental enteropathy results in a number of changes in the intestines including: reduced Villus height, larger and fewer crypts, increased permeability, and inflammatory cell build-up within the intestines. These changes result in poor absorption of food, vitamins and minerals—or "modest malabsorption."

Cancer Induced Weight Loss. Weight loss is common among people with cancer and is often the first noticeable sign of the disease. a substantial percentage of people with cancer report unexplained weight loss at the time of diagnosis, and the majority of people with advanced cancer experience weight loss or wasting, which is the combination of weight loss and muscle mass loss. Weight loss and muscle wasting also often come with fatigue, weakness, loss of energy, and an inability to perform everyday tasks.

Norovirus Symptoms. Norovirus is a highly contagious virus. People contract the virus by ingesting material contaminated with small amounts of infected feces or fluids. Food and water may be contaminated during processing or handling. Norovirus causes inflammation of the stomach or intestines or both and is the most common cause of gastroenteritis in the United States. The most common symptoms are diarrhea, vomiting, nausea and stomach pain.

Food Poisoning Symptoms. Food poisoning refers to any illness resulting from the consumption of contaminated food, pathogenic bacteria, viruses, or parasites that contaminate food, as well as chemical or natural toxins such as poisonous mushrooms. More than 250 different diseases can cause food poisoning. Some of the most common diseases are infections caused by bacteria, such as *Campylobacter, Salmonella, Shigella, E. coli* 0157:H7, *Listeria*, Botulism, and Norovirus. A common symptom of food poisoning is diarrhea.

Wound Symptoms. There are many types of wounds that can damage the skin including abrasions, lacerations, rupture injuries, punctures, and penetrating wounds. The purpose of medical care for wounds is to prevent complications and preserve function. Inflammation is the skin's initial response to injury.

BRIEF SUMMARY

The subject invention provides therapeutic compositions and methods for improving small intestine function. The subject composition is useful for the treatment or amelioration of gastrointestinal injury associated with the loss of small intestine epithelial cells, particularly in the Villus region and the brush border, and/or for the treatment or amelioration of diseases or conditions associated with the alteration of absorptive capacity in the small intestine.

Advantageously, the subject therapeutic composition can be tailored to the misbalanced absorptive state of the gastrointestinal system caused by the loss of small intestine epithelial cells and the alteration of transport protein function in the small intestine. In a preferred embodiment, the subject composition is formulated for oral administration.

In one embodiment, the therapeutic composition comprises, consists essentially of, or consists of, one or more free amino acids selected from lysine, glycine, threonine, valine, tyrosine, aspartic acid, isoleucine, tryptophan, asparagine, and serine; and optionally, therapeutically acceptable carriers, electrolytes, vitamins, buffering agents, and flavoring agents. The therapeutic composition is administered via an enteral route. In one embodiment, the total osmolarity of the composition is from about 230 mosm to 280 mosm, or preferably, about 250 to 260 mosm. In one embodiment, the composition has a pH from about 7.1 to 7.9, preferably, about 7.4.

In a specific embodiment, the composition of the subject invention does not comprise glucose, glutamine, methionine, and/or lactose.

Also provided are methods for treatment or amelioration of diseases or symptoms associated with the loss of small intestine epithelial cells, particularly in the Villus region and brush border, and diseases or symptoms associated with the alteration of transport protein function in the small intestine epithelium. The method comprises administering, via an enteral route, to a subject in need of such treatment, an effective amount of the composition of the subject invention. Preferably, the subject composition is administered orally and reaches the intestine of the subject.

The subject invention also provides methods for preparing the therapeutic composition, and for screening for nutrients or electrolytes for inclusion into the subject therapeutic/dietary composition, by selecting nutrients or electrolytes that retain or acquire considerable absorptive capacity following the destruction of small intestine epithelial cells. These methods can be adapted for use in individual patients, thereby facilitating the development of compositions and methods specifically designed to meet the needs of an individual patient.

Also provided are compositions and methods for treating a subject having Ebola virus infection comprising administering to the subject, a composition comprising one or more ingredients selected from lysine, glycine, threonine, tryptophan, valine, treosine, serine, and tyrosine, as free amino acids or a combination thereof; wherein the composition does not comprise free amino acid glutamine or a glutamine-containing dipeptide; wherein the composition does not comprise glucose or, if glucose is present, the concentration of glucose is less than 1 g/l; and wherein the composition does not comprises methionine or a methionine-containing dipeptide.

Also provided is a method for treating a subject having HIV infection comprising administering to the subject a composition comprising one or more ingredients selected from lysine, glycine, threonine, tryptophan, valine, treosine, serine, and tyrosine, as free amino acids or a combination thereof; wherein the composition does not comprise free amino acid glutamine or a glutamine-containing dipeptide; wherein the composition does not comprise glucose or, if glucose is present, the concentration of glucose is less than 1 g/l; and wherein the composition does not comprises methionine or a methionine-containing dipeptide.

Also provided is a method for treating a subject having ataxia symptoms comprising administering to the subject a composition comprising at least one amino acid that retains or acquires improved absorptive capacity following the impairment of small intestine epithelial cells, the amino acids selected from the group consisting of lysine, glycine, serine, threonine, tryptophan, valine, and tyrosine, as free amino acids; one or more electrolyte selected from among the group consisting of sodium, potassium, magnesium and calcium and wherein the composition does not comprise free amino acid glutamine or a glutamine-containing dipeptide, or, if free amino acid glutamine and/or a glutamine-containing dipeptide is present, the total concentration of the free amino acid glutamine and the glutamine-containing dipeptide is less than 300 mol and wherein the composition does not comprise glucose or, if glucose is present, the concentration of glucose is less than IU.

Also provided is a method for treating a subject having decreased Villus height comprising administering to the subject a composition comprising an amino acid that retains or acquires improved absorptive capacity following the impairment of small intestine epithelial cells, the amino acids selected from the group consisting of lysine, glycine, threonine, tryptophan, serine, valine, and tyrosine, as free amino acids; and wherein the composition does not comprise free amino acid glutamine or a glutamine-containing dipeptide, or, if free amino acid glutamine and/or a glutamine-containing dipeptide is present, the total concentration of the free amino acid glutamine and the glutamine-containing dipeptide is less than 300 mol and wherein the composition does not comprise glucose or, if glucose is present, the concentration of glucose is less than IU.

Also provided is a method for the treatment of environmental enteropathy comprising administering to the subject a composition comprising an amino acid selected from the group consisting of lysine, glycine, threonine, serine, tryptophan, valine, and tyrosine, as free amino acids; and wherein the composition does not comprise free amino acid glutamine or a glutamine-containing dipeptide, or, if free amino acid glutamine and/or a glutamine-containing dipeptide is present, the total concentration of the free amino acid glutamine and the glutamine-containing dipeptide is less than 300 mol and wherein the composition does not comprise glucose or, if glucose is present, the concentration of glucose is less than IU.

Also provided is a method for the treatment of weight loss caused by cancer comprising administering to the subject a composition comprising an amino acid selected from the group consisting of lysine, glycine, threonine, serine, tryptophan, valine, and tyrosine, as free amino acids; and wherein the composition does not comprise free amino acid glutamine or a glutamine-containing dipeptide, or, if free amino acid glutamine and/or a glutamine-containing dipeptide is present, the total concentration of the free amino acid glutamine and the glutamine-containing dipeptide is less than 300 mol and wherein the composition does not comprise glucose or, if glucose is present, the concentration of glucose is less than IU.

DETAILED DISCLOSURE

The compositions disclosed herein work in disease conditions associated with reduced absorptive capacity (inhibition of electroneutral sodium and chloride absorption and/or Villus damage), enhanced chloride secretion, increased intestinal permeability and microbial translocation, chronic systemic inflammation and diarrhea.

Reduced intestinal nutrient and electrolyte absorption associated with decreased Villus height further exacerbates GI toxicity. The presence of unabsorbed nutrients and electrolytes in the gut lumen lead to osmotic diarrhea. Some nutrients, such as glucose and specific amino acids (AAs) (Arginine, histidine, methionine, phenylalanine, leucine, alanine, asparagine, cysteine, glutamine, glutamic acid), activate active anion secretion and/or increase paracellular permeability (Health Phys., 106(6):734-44, 2014). These nutrients were not included in the formulation of the invention. In addition some of the nutrients e.g., glucose was shown to increase chloride secretion secondary to increased intracellular calcium (Am. J. Physiol. Cell Physiol., 2014; 306(7):C687-C697). Glucose-stimulated active chloride secretion becomes more critical in situations associated with Villus atrophy as glucose and some of the nutrient absorption occurs in the fully differentiated and mature Villus tip.

In preclinical studies using irradiated mice treated with an oral mixture of the correct AAs; lysine, aspartic acid, glycine, isoleucine, threonine, tyrosine, valine, tryptophan, serine decreased the paracellular permeability, plasma endotoxin and pro-inflammatory cytokine levels, and mortality in mice exposed to lethal dose of irradiation (13Gy TBI) (Health Phys., 106(6):734-44, 2014).

In preclinical and in human subjects the compositions disclosed herein provided benefits in distant organs such as the lung. The compositions disclosed herein improved the lung function and radiological clearance. The compositions contain a selection of amino acids and electrolytes that are included in the generally recognized as safe (GRAS) list, suggesting that it would pose minimal risk in the form of toxicity.

Treatment of Alcohol Hangovers

In one embodiment, the compositions disclosed herein are used in a method for the treatment of hangovers. Symptoms of hangovers can be attributed to a buildup of acetaldehyde in the body. Some common hangover symptoms such as fatigue, stomach irritation and a general sense of illness can be further attributed to glutamine rebound. Consumption of alcohol inhibits glutamine. When the drinker stops drinking, the body produces more glutamine than it needs. Increased glutamine levels stimulate the brain leading to a loss of sleep leading to the fatigue associated with a hangover. Increased amounts of glutamine may also cause tremors, anxiety, restlessness and increased blood pressure. Alcohol consumption can damage the intestinal epithelial cells. In addition, alcohol increases paracellular permeability (leaky gut).

Because alcohol is absorbed directly through the stomach, the cells that line the organ become irritated. The stomach's irritation may also be a factor in some of the other unpleasant symptoms of a hangover, such as diarrhea and lack of appetite. Additionally, alcohol is a diuretic in one of the consequences of heavy alcohol consumption is dehydration. Cysteine breaks down the hangover-causing toxin acetaldehyde in the liver's easily depleted glutathione. Replenishment of potassium lost to alcohol's diuretic effect is also desirable.

A composition for the treatment of hangover may include one or more of the following constituents:
lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l,
or a subset of these ingredients. In other embodiments the composition may include two or more of the disclosed amino acids. The composition does not contain glutamine, glucose or carbohydrates that can hydrolyze into glucose in the gut. The composition increased electrolyte absorption and improved mucosal barrier functions. The amino acid composition provide for the regulation of calcium-mediated chloride secretion in the intestinal epithelium. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acids help move fluid into the fluid compartments and therefore form a complete rehydration mechanism.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In other embodiments the composition may include two or more of the disclosed amino acids.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

In other embodiments the composition may include two or more of the disclosed amino acids.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity following excessive alcohol consumption alleviates an array of symptoms associated with hangovers including, but not limited to, one or more of the following: fatigue, thirst, headaches and muscle aches, nausea, vomiting or stomach pain, poor or decreased sleep, increased sensitivity to light and sound, dizziness or a sense of the room spinning, rapid heartbeat, red, bloodshot eyes, shakiness, decreased ability to concentrate, and mood disturbances, such as depression, anxiety and irritability.

The amino acids help move fluid into the three fluid compartments and therefore form a complete rehydration mechanism. In one embodiment the therapeutic composition may be administered via a parenteral route such as intravenously.

In one embodiment the composition for the treatment of hangover may be provided in powder or pill form.

In one embodiment a method for the treatment of hangovers or alcohol toxicity comprises administering to the subject, the composition described above.

Treatment of Inflammation

Inflammation is part of the response of vascular tissues to harmful stimuli, such as pathogens, damaged cells, irritants or inflammatory diseases. Inflammation is the protective attempt by the body to remove the damaging stimuli and to trigger the healing process.

A composition for the treatment of inflammation may include one or more of the following constituents:

lysine at a concentration of about 730 to 6575 mg/l;

aspartic acid at a concentration of about 532 to 4792 mg/l;

glycine at a concentration of about 300 to 2703 mg/l;

isoleucine at a concentration of about 525 to 4722 mg/l;

threonine at a concentration of about 476 to 4288 mg/l;

tyrosine at a concentration of about 725 to 6523 mg/l;

valine at a concentration of about 469 to 4217 mg/l;

tryptophan at a concentration of about 817 to 7352 mg/l;

asparagine at a concentration of about 528 to 4756 mg/l; and/or serine at a concentration of about 420 to 3784 mg/l, or a subset of these ingredients. In other embodiments the composition may include two or more of the disclosed amino acids. The amino acid compositions work by correcting the cell shrinkage that occurs secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The composition does not contain glutamine, glucose or carbohydrates that can hydrolyze into glucose in the gut.

In another preferred embodiment, the composition for the treatment of inflammation may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In other embodiments the composition may include two or more of the disclosed amino acids. In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L and tryptophan at a concentration of between about 100 mg/L-gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L The composition can be used to treat inflammation that is local (limited to the intestinal tissues) or systemic. The amino acid mixture ameliorates both types of inflammation.

The subject invention is based, at least in part, on the discovery that enteral feeding to subjects with only the nutrients that retain or acquire sufficient absorptive capacity in cases of inflammation alleviates an array of symptoms associated with inflammation including, but not limited to one or more of the following: pain in the joints or muscles, allergies, asthma, high blood pressure, blood sugar problems, ulcers and Irritable Bowel Syndrome (constipation or diarrhea), constant fatigue or lethargy, skin problems or red, bloodshot eyes, edema, hyperemia, erythema, bruising, fluid retention, loss of appetite, increased heart rate, formation of granulomas, fibrinous, pus, or nonviscous serous fluid, and formation of an ulcer.

In one embodiment the therapeutic composition may be administered via a parenteral route such as intravenously. In one embodiment the composition for the treatment of inflammation may be provided in powder or pill form.

In one embodiment a method for the treatment of inflammation comprises administering to the subject, the composition described above.

Electrolyte Replacement

Electrolytes are certain minerals (e.g., calcium, bicarbonate chloride, magnesium, manganese, phosphate, potassium, and sodium ions) essential to human health. As an essential mineral, an electrolyte cannot be substituted by any other nutrient in the diet. It has been established that during strenuous exercise, significant amounts of electrolytes are eliminated, which may account for systemic losses of Na+, Cl−, K+, Ca++, and HCO3− Electrolyte losses may contribute to early exhaustion, fatigue, muscle cramps, cardiac effects (arrhythmias) and CNS effects (asthenia).

An electrolyte replacement composition may be formulated as a beverage comprising electrolytes such as sodium, chloride, bicarbonate, calcium, phosphate, manganese, magnesium, and potassium. In one embodiment an electrolyte replacement composition may include:

sodium ion (preferentially as chloride) not more than 250 mg/L;

potassium ion (preferentially as phosphate) not less than 100 mg/L;

magnesium (as any nutritionally acceptable salt) not less than 100 mg/L;

zinc (as any nutritionally acceptable salt) not more than 30 mg/L;

manganese (as any nutritionally acceptable complex) not more than 10 mg/L;

calcium (as any nutritionally acceptable salt) between 65 and 400 mg/L; and one or more free amino acids selected from lysine, glycine, threonine, threonine, valine, tyrosine, aspartic acid, isoleucine, tryptophan, asparagine, and serine; and optionally, therapeutically acceptable carriers, vitamins, buffering agents, and flavoring agents.

In other embodiments the composition may include two or more of the disclosed amino acids. In other embodiments the composition may include two or more of the disclosed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability.

The beverage will not contain glucose or a carbohydrate that may be hydrolyzed into glucose in the gut.

The beverage will also not contain glutamine, cysteine, methionine, and/or lactose.

The total osmolarity of the beverage composition is from about 230 mosm to 280 mosm, or preferably, is about 250 to 260 mosm.

The composition is formulated so that when the ingested composition is in contact with the villous and brush border of the small bowel the pH is between 7.1 to 7.9, or any value therebetween. Preferably, when the ingested composition is in contact with the villous and brush border of the small bowel the composition has a pH from about 7.3 to 7.5, more preferably, about 7.4. In some embodiments the beverage composition may have a pH of between 3-8, provided that when the ingested composition is in contact with the villous and brush border of the small bowel the pH is between 7.1 to 7.9.

In certain specific embodiments, the amino acid component of the therapeutic composition comprises one or more free amino acids present at their respective concentrations as follows:

lysine at a concentration of about 730 to 6575 mg/l;

aspartic acid at a concentration of about 532 to 4792 mg/l;

glycine at a concentration of about 300 to 2703 mg/l;

isoleucine at a concentration of about 525 to 4722 mg/l;

threonine at a concentration of about 1 to 10,000 mg/L;

threonine at a concentration of about 476 to 4288 mg/l;

tyrosine at a concentration of about 725 to 6523 mg/l;

valine at a concentration of about 469 to 4217 mg/l;

tryptophan at a concentration of about 817 to 7352 mg/l;

asparagine at a concentration of about 528 to 4756 mg/l; and/or serine at a concentration of about 420 to 3784 mg/l, The total osmolarity of the composition is from about 240 mosm to 280 mosm.

In another preferred embodiment, the electrolyte replacement composition may comprise a combination of one or more of the following amino acids:— threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L and.

tryptophan at a concentration of between about 1 mg/L-10 mg/L

In one embodiment the formulation may be formulated for parenteral administration such as intravenously.

In a more preferred embodiment the electrolyte replacement composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the electrolyte replacement composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L and tryptophan at a concentration of between about 0.5 gm/L-2 gm/L.

The presence of the free amino acids provides a more effective transport of the electrolytes into the body. It was found that there was an increase in electrolyte and nutrient absorption secondary to increase in villous height (increasing the surface area of absorption) in irradiated and non-irradiated mice treated with the four amino acids mixture for a period of time as short as four days.

In one embodiment a method for the replacement of electrolytes comprises administering to the subject, the electrolyte replacement composition described above.

Rehydration Composition

Strenuous exercise places a metabolic demand on the human body. One of the consequences of strenuous exercise is the loss of sweat which can result in dehydration. The resulting loss of water and electrolytes causes fatigue. Commercial fluid replacement drinks often contain glucose or fructose, as a supplementary energy source. It has been found that as the carbohydrate concentration of a drink increases, the rate of fluid replacement to the body is decreased.

A rehydration composition may be formulated as a beverage comprising:

sodium ion (preferentially as chloride) not more than 250 mg/L;

potassium ion (preferentially as phosphate) not less than 100 mg/L;

magnesium (as any nutritionally acceptable salt) not less than 100 mg/L;

zinc (as any nutritionally acceptable salt) not more than 30 mg/L;

manganese (as any nutritionally acceptable complex) not more than 10 mg/L;

calcium (as any nutritionally acceptable salt) between 65 and 400 mg/L; and one or more free amino acids selected from lysine, glycine, threonine, valine, tyrosine, aspartic acid, isoleucine, tryptophan, asparagine, and serine; and optionally, therapeutically acceptable carriers, vitamins, buffering agents, and flavoring agents.

In other embodiments the composition may include two or more of the disclosed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability.

The beverage will not contain glucose or a carbohydrate that may be hydrolyzed into glucose in the gut.

The beverage will also not contain glutamine, cysteine, methionine, and/or lactose.

The total osmolarity of the beverage composition is from about 230 mosm to 280 mosm, or preferably, is about 250 to 260 mosm.

In certain specific embodiments, the amino acid component of the rehydration composition comprises one or more free amino acids present at their respective concentrations as follows:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l,
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l, The total osmolarity of the composition is from about 240 mosm to 280 mosm.

In another preferred embodiment, the rehydration beverage may comprise a combination of threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the rehydration beverage may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the rehydration beverage may comprise a combination of one or more of the following amino acids:

threonine at a concentration of between about 0.5 gm/L-gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The presence of the free amino acids provides a more effective transport of the electrolytes into the body. The amino acids help to move fluid into the three fluid compartments and therefore form a complete rehydration mechanism.

In one embodiment the rehydration beverage has a pH of between 2.9 to 7.6 and preferably a pH of between 3.8 in-4.5.

In one embodiment a rehydration composition is provided with the foregoing amino acid compositions provided in powder or pill form.

In one embodiment a method for rehydration comprises administering to the subject, the rehydration composition or rehydration beverage described above.

Nutrient Delivery

Absorption of a nutrient is dependent on the food-calorie content, composition, volume, temperature of diet, amount of fluid ingested, and the fed status. Nutrients have the potential to alter gastrointestinal pH, motility, secretions, flora, and mucosal morphology or function and can consequently be absorbed in higher or lower amounts.

In certain specific embodiments, the amino acid component of the therapeutic composition for enhanced nutrient delivery comprises one or more free amino acids present at their respective concentrations as follows:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 1 to 10,000 mg/L;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l.

The total osmolarity of the composition is from about 240 mosm to 280 mosm. In other embodiments the composition may include two or more of the disclosed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular—compartment to restore the intracellular fluid volume and decrease the cell shrinkage and therefore paracellular permeability In another preferred embodiment, the therapeutic composition for enhanced nutrient delivery may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the therapeutic composition for enhanced nutrient delivery may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the therapeutic composition for enhanced nutrient delivery may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

In one embodiment the formulation may be formulated for parenteral administration such as intravenously.

Beverage for Geriatric Population

Older subjects often suffer from protein caloric malnutrition. The ability of older adults to effectively control energy intake is affected because of the delayed rate of absorption of macronutrients. Older adults have a decreased capacity to absorb nutrients such as vitamin B12 and vitamin D.

The DRIs for older adults from the Food and Nutrition Board of the Institute of Medicine are as follows for each age group.

| Male ages 51 to 70, per day | Female ages 51 to 70, per day | Male age 71 or older, per day | Female age 71 or older, per day |
|---|---|---|---|
| VIT A, 900 mcg | VIT A, 700 mcg | VIT A, 900 mcg | VIT A, 700 mcg |
| VIT C, 90 mg | VIT C, 75 mg | VIT C, 90 mg | VIT C, 75 mg |

-continued

| Male ages 51 to 70, per day | Female ages 51 to 70, per day | Male age 71 or older, per day | Female age 71 or older, per day |
|---|---|---|---|
| VIT D, 15 mcg | VIT D, 15 mcg | VIT D, 20 mcg | VIT D, 20 mcg |
| VIT E, 15 mg | VIT E, 15 mg | VIT E, 15 mg | VIT E, 15 mg |
| VIT B6, 1.5 mg | VIT B6, 1.5 mg | VIT B6, 1.7 mg | VIT B6, 1.5 mg |
| VIT B12, 2.4 mcg | VIT B12, 2.4 mcg | VIT B12, 2.4 mcg | VIT B12, 2.4 mcg |
| Folate, 400 mcg | Folate, 400 mcg | Folate, 400 mcg | Folate, 400 mcg |
| Ikon, 8 mg | Iron, 8 mg | Iron, 8 mg | Iron, 8 mg |
| Calcium, 1,000 mg | Calcium, 1,200 mg | Calcium, 1,200 mg | Calcium, 1,200 mg |
| Niacin, 14 mg | Niacin, 14 mg | Niacin, 16 mg | Niacin, 14 mg |

In one embodiment of the invention a nutritional composition for a geriatric population may include proteins, fats, minerals and Vitamins and free amino acids selected from the group consisting of lysine (11-21 mosm), aspartic acid (3-13 mosm), glycine (19-29 mosm), isoleucine (19-29 mosm), threonine (19-29 mosm), tyrosine (0.5-5 mosm), valine (19-29 mosm), tryptophan (5-20 mosm), asparagine (3-13 mosm), and serine (3-8 mosm), or a subset of these ingredients. The composition will preferably not contain glutamine or cysteine. The composition will preferably not contain glucose or carbohydrates that can hydrolyze into glucose in them.

In another embodiment a nutritional composition for a geriatric population may include one or more free amino acids present at their respective concentrations as follows:
  lysine at a concentration of about 730 to 6575 mg/l;
  aspartic acid at a concentration of about 532 to 4792 mg/l;
  glycine at a concentration of about 300 to 2703 mg/l;
  isoleucine at a concentration of about 525 to 4722 mg/l;
  threonine at a concentration of about 1 to 10,000 mg/L;
  threonine at a concentration of about 476 to 4288 mg/l;
  tyrosine at a concentration of about 725 to 6523 mg/l;
  valine at a concentration of about 469 to 4217 mg/l;
  tryptophan at a concentration of about 817 to 7352 mg/l;
  asparagine at a concentration of about 528 to 4756 mg/l;
and/or
  serine at a concentration of about 420 to 3784 mg/l.
In other embodiments the composition may include two or more of the disclosed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability In another preferred embodiment, the nutritional composition for a geriatric population may comprise a combination of one or more of the following amino acids:
  threonine at a concentration of between about 1 mg/L-10 mg/L,
  tyrosine at a concentration of between about 1 mg/L-10 mg/L,
  serine at a concentration of between about 1 mg/L-10 mg/L,
  valine at a concentration of between about 1 mg/L-10 mg/L, and
  tryptophan at a concentration of between about 1 mg/L-10 mg/L.

In a more preferred embodiment the nutritional composition for a geriatric population may comprise a combination of one or more of the following amino acids:
  threonine at a concentration of between about 100 mg/L-5 gm/L,
  tyrosine at a concentration of between about 100 mg/L-5 gm/L,
  serine at a concentration of between about 100 mg/L-5 gm/L,
  valine at a concentration of between about 100 mg/L-5 gm/L, and
  tryptophan at a concentration of between about 100 mg/L-5 gm/L.

In a most preferred embodiment the nutritional composition for a geriatric population may comprise a combination of one or more of the following amino acids:
  threonine at a concentration of between about 0.5 gm/L-2 gm/L,
  tyrosine at a concentration of between about 0.5 gm/L-2 gm/L,
  serine at a concentration of between about 0.5 gm/L-2 gm/L,
  valine at a concentration of between about 0.5 gm/L-2 gm/L, and
  tryptophan at a concentration of between about 0.5 gm/L-2 gm/L.

The composition of the foregoing embodiment provides for enhanced absorption of nutrients as a result of the presence of the free amino acids.

In one embodiment a method for delivering nutrition to a geriatric patient comprises administering to the subject, the nutritional composition described above.

Drug Delivery System

During drug delivery, drugs must pass or permeate through epithelial cells in order to be absorbed into the circulatory system. One particular cellular barrier that may prevent absorption of a given drug is the cell membrane. Cell membranes are essentially lipid bilayers which form a semipermeable membrane. Pure lipid bilayers are generally permeable only to small, uncharged solutes. Ionization of a molecule will affect its absorption, since ionic molecules are charged. Solubility favors charged species, and permeability favors neutral species. Some molecules have special exchange proteins and channels to facilitate movement from the lumen into the circulation.

A composition to augment drug delivery and enhance pharmacokinetics thereby enhancing drug availability may include one or more of the following constituents:
  lysine at a concentration of about 730 to 6575 mg/l;
  aspartic acid at a concentration of about 532 to 4792 mg/l;
  glycine at a concentration of about 300 to 2703 mg/l;

isoleucine at a concentration of about 525 to 4722 mg/l;
threonine at a concentration of about 1 to 10,000 mg/L;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l,
or a subset of these ingredients. The composition does not contain glutamine, glucose or carbohydrates that can hydrolyze into glucose in the gut. In other embodiments the composition may include two or more of the disclosed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability In another preferred embodiment, the composition to augment drug delivery and enhance pharmacokinetics may comprise a combination of one or more of the following amino acids:
threonine at a concentration of between about 1 mg/L-10 mg/L,
tyrosine at a concentration of between about 1 mg/L-10 mg/L,
serine at a concentration of between about 1 mg/L-10 mg/L,
valine at a concentration of between about 1 mg/L-10 mg/L, and
tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:
threonine at a concentration of between about 100 mg/L-5 gm/L,
tyrosine at a concentration of between about 100 mg/L-5 gm/L,
serine at a concentration of between about 100 mg/L-5 gm/L,
valine at a concentration of between about 100 mg/L-5 gm/L, and
tryptophan at a concentration of between about 100 mg/L-5 gm/L.

In a most preferred embodiment the composition may comprise a combination of one or more of the following amino acids:
threonine at a concentration of between about 0.5 gm/L-2 gm/L,
tyrosine at a concentration of between about 0.5 gm/L-2 gm/L,
serine at a concentration of between about 0.5 gm/L-2 gm/L,
valine at a concentration of between about 0.5 gm/L-2 gm/L and
tryptophan at a concentration of between about 0.5 gm/L-2 gm/L.

In one embodiment the composition to augment drug delivery and enhance pharmacokinetics thereby enhancing drug availability may be delivered in powder or pill form.

In one embodiment a method for enhancing drug delivery comprises administering to the subject, the composition to augment drug delivery and enhance pharmacokinetics described above.

Treatment of Dehydration Caused by Diabetes

People with diabetes have an increased risk of dehydration as high blood glucose levels lead to decreased hydration in the body. Diabetes insipidus, a form of diabetes that is not linked with high blood sugar levels, also carries a higher risk of dehydration. If blood glucose levels are higher than normal for a prolonged period of time, the kidneys will attempt to remove some of the excess glucose from the blood and excrete this as urine. When the kidneys lose the glucose through the urine, a large amount of water is also lost, causing dehydration. When a person with type 2 diabetes becomes severely dehydrated and is not able to drink enough fluids to make up for the fluid losses, they may develop Hyperosmolar nonketotic diabetic coma, a life-threatening complication.

In one embodiment, the compositions disclosed herein are used in a method for the treatment of dehydration caused by diabetes.

A composition for the treatment of dehydration caused by diabetes may include one or more of the following constituents:
lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 1 to 10,000 mg/L;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l,
or a subset of these ingredients. The composition does not contain glutamine, glucose or carbohydrates that can hydrolyze into glucose in the gut. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability In other embodiments the composition may include two or more of the disclosed amino acids.

In another preferred embodiment, the composition may comprise a combination of one or more of the following amino acids:
threonine at a concentration of between about 1 mg/L-10 mg/L,
tyrosine at a concentration of between about 1 mg/L-10 mg/L,
serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L 2 gm/L, serine at a concentration of between about 0.5 gm/L-2 gm/L, valine at a concentration of between about 0.5 gm/L-2 gm/L and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity in cases of diabetes improves mucosal healing, restores small intestine function, enhances fluid retention, and alleviates an array of associated disease symptoms including, but not limited to, malabsorption, diarrhea, nausea, vomiting, electrolyte imbalance, and dehydration.

In one embodiment the composition for the treatment of dehydration caused by diabetes may be delivered in powder or pill form.

In one embodiment a method for the treatment of dehydration caused by diabetes comprises administering to the subject, the composition for the treatment of dehydration caused by diabetes described above.

Treatment of Porcine Epidemic Diarrhea

In one embodiment, the compositions disclosed herein are used in a method for the treatment of Porcine epidemic diarrhea. Porcine Epidemic Diarrhea Virus (PEDV) is a coronavirus that infects the cells lining the small intestine of a pig, causing porcine epidemic diarrhea, a condition of severe diarrhea and dehydration. Older hogs mostly get sick and lose weight after being infected, whereas newborn piglets usually die within five days of contracting the virus. PEDV cannot be transmitted to humans, nor contaminate the human food supply.

In a field trial with 10 piglets, all infected with the PEDV where 5 piglets were treated with the composition described below it was found that the 5 piglets treated with the composition all survived while the five piglets not treated all died.

A composition for the treatment of porcine epidemic diarrhea may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l, or a subset of these ingredients. In other embodiments the composition may comprise two or more of the listed amino acids. The composition does not contain glutamine, glucose or carbohydrates that can hydrolyze into glucose in the gut. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity following infection with PEDV.

In one embodiment the composition for the treatment of porcine epidemic diarrhea may be delivered in powder or pill form.

In one embodiment a method for the treatment of porcine epidemic diarrhea comprises administering to the subject, one of the compositions for the treatment of porcine epidemic diarrhea described above.

Treatment of Environmental Enteropathy

Environmental enteropathy is a subclinical condition caused by constant fecal-oral contamination and resulting in blunting of intestinal villi and intestinal inflammation. Environmental enteropathy may cause the failure of nutritional interventions and oral vaccines. Environmental enteropathy may result in increased intestinal permeability, malabsorption, impaired gut immune function, and oral vaccine failure.

In one embodiment, the compositions disclosed herein are used in a method for the treatment of environmental enteropathy.

A composition for the treatment of environmental enteropathy may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l, or a subset of these ingredients. The composition does not contain glutamine, glucose or carbohydrates that can hydrolyze into glucose in the gut. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity in cases of environmental enteropathy improves mucosal healing, restores small intestine function, enhances fluid retention, and alleviates an array of associated disease symptoms including, but not limited to, malabsorption, diarrhea, nausea, vomiting, electrolyte imbalance, and dehydration.

In one embodiment the composition for the treatment of environmental enteropathy may be delivered in powder or pill form.

In one embodiment a method for the treatment of environmental enteropathy comprises administering to the subject, one of the compositions for the treatment of environmental enteropathy described above.

Augmentation of Immunization Efficiencies

Immunization is a process by which the immune system becomes fortified against an agent. When the immune system is exposed to foreign molecules it will develop an immune response, and it will also develop the ability to quickly respond to a subsequent encounter because of immunological memory. This is a function of the adaptive immune system. T lymphocytes, B lymphocytes, and the antibodies B lymphocytes produce memory B lymphocytes and memory T lymphocytes that are responsible for the immune system response to a second encounter with a foreign molecule. Passive immunization is when these elements are introduced directly into the body, instead of when the body itself has to make these elements.

A composition for augmenting immunization efficiencies includes one or more of the following constituents:
lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 1 to 10,000 mg/L;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l,
or a subset of these ingredients. In other embodiments the composition comprises two or more of the listed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut.

In another preferred embodiment, the composition to improve immunization efficiencies may comprise a combination of one or more of the following amino acids:
threonine at a concentration of between about 1 mg/L-10 mg/L,
tyrosine at a concentration of between about 1 mg/L-10 mg/L,
serine at a concentration of between about 1 mg/L-10 mg/L,
valine at a concentration of between about 1 mg/L-10 mg/L and
tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:
threonine at a concentration of between about 100 mg/L-5 gm/L,
tyrosine at a concentration of between about 100 mg/L-5 gm/L,
serine at a concentration of between about 100 mg/L-5 gm/L,
valine at a concentration of between about 100 mg/L-5 gm/L. and
tryptophan at a concentration of between about 100 mg/L-5 gm/L.

In a most preferred embodiment the composition may comprise a combination of one or more of the following amino acids:
threonine at a concentration of between about 0.5 gm/L-2 gm/L,
tyrosine at a concentration of between about 0.5 gm/L-2 gm/L,
serine at a concentration of between about 0.5 gm/L-2 gm/L,
valine at a concentration of between about 0.5 gm/L-2 gm/L and
tryptophan at a concentration of between about 0.5 gm/L-2 gm/L.

In one embodiment the composition to improve immunization efficiencies may be delivered in powder or pill form.

In one embodiment a method for augmenting immunization efficiencies comprises administering to the subject, one of the compositions for the improvement of immunization efficiencies described above.

Treatment of the Effects of Irradiation

Gastrointestinal toxicity can occur following irradiation of abdominal or other malignancies in cases where normal gastrointestinal structures are located within the radiation therapy (RT) field. These toxicities may limit the maximum dose of RT and chemotherapy. Side effects of RT include early (acute) toxicity, such as diarrhea and nausea.

A composition for the treatment of the effects of irradiation includes one or more of the following constituents:
lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l,
or a subset of these ingredients. In other embodiments the composition comprises two or more of the listed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut.

In another preferred embodiment, the composition for the treatment of the effects of irradiation may comprise a combination of one or more of the following amino acids:
threonine at a concentration of between about 1 mg/L-10 mg/L,
tyrosine at a concentration of between about 1 mg/L-10 mg/L,
serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L and tryptophan at a concentration of between about 0.5 gm/L-2 gm/L.

It was found that there was an increase in the crypt number, crypt height, villous length and villous number in irradiated and non-irradiated mice treated with the amino acids mixture for a period of time as short as four days.

In one embodiment the composition for the treatment of the effects of irradiation may be delivered in powder or pill form.

In one embodiment a method for the treatment the effects of irradiation comprises administering to the subject, one of the compositions for the treatment of the effects of irradiation described above.

Treatment of Ebola Symptoms

In one embodiment the composition decreases stool volume and frequency in acute diarrheal situations, rapidly corrects dehydration and tightens the mucosal barrier. Such effects are effective in correcting the fluid loss in patients with Ebola virus.

A composition for the treatment of Ebola virus infection symptoms may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l, or a subset of these ingredients. In other embodiments the composition comprises two or more of the listed amino acids. The amino acid compositions work by correcting the cell shrinkage that occur secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

In one embodiment a method for the treatment of symptoms of Ebola virus infection comprises administering to the subject, one of the compositions for the treatment of Ebola virus infection described above.

Treatment of HIV Symptoms

In one embodiment, the compositions disclosed herein are used in a method for the treatment of HIV infection symptoms.

A composition for the treatment of HIV infection symptoms may include one or more of the following constituents:
lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l,
or a subset of these ingredients. In other embodiments the composition comprises two or more of the listed amino acids. The amino acid compositions work by correcting the cell shrinkage that occurs secondary to chloride secretions, and thus correct muscosal barrier defect and downstream local and systemic inflammation. The amino acid composition initially rehydrates the vascular and interstitial fluid compartments of the cells in the gut. Subsequently, the amino acid composition rapidly rehydrate the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:
threonine at a concentration of between about 1 mg/L-10 mg/L,
tyrosine at a concentration of between about 1 mg/L-10 mg/L,
serine at a concentration of between about 1 mg/L-10 mg/L,
valine at a concentration of between about 1 mg/L-10 mg/L, and
tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:
threonine at a concentration of between about 100 mg/L-5 gm/L,
tyrosine at a concentration of between about 100 mg/L-5 gm/L,
serine at a concentration of between about 100 mg/L-5 gm/L,
valine at a concentration of between about 100 mg/L-5 gm/L, and
tryptophan at a concentration of between about 100 mg/L-5 gm/L.

In a most preferred embodiment the composition may comprise a combination of one or more of the following amino acids:
threonine at a concentration of between about 0.5 gm/L-2 gm/L,
tyrosine at a concentration of between about 0.5 gm/L-2 gm/L,
serine at a concentration of between about 0.5 gm/L-2 gm/L,
valine at a concentration of between about 0.5 gm/L-2 gm/L, and
tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity alleviates symptoms associated with HIV infection.

In one embodiment a method for the treatment of HIV symptoms comprises administering to the subject, one of the compositions for the treatment of HIV symptoms described above.

Treatment of Ataxia Symptoms

In one embodiment, the compositions disclosed herein are used in a method for the treatment of Ataxia symptoms.

A composition for the treatment of Ataxia symptoms may include one or more of the following constituents:
lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l,
or a subset of these ingredients. In other embodiments the composition comprises two or more of the listed amino acids. The amino acid compositions work by correcting the cell shrinkage that occurs secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:
threonine at a concentration of between about 1 mg/L-10 mg/L,
tyrosine at a concentration of between about 1 mg/L-10 mg/L,
serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity alleviates symptoms associated with Ataxia.

In one embodiment a method for the treatment of Ataxia symptoms comprises administering to the subject, one of the compositions for the treatment of Ataxia symptoms described above.

Method for Increasing Villus Height and Crypt Number

In one embodiment, the compositions disclosed herein are used in a method for increasing Villus height and crypt numbers.

A composition to promote the increase of Villus height and crypt numbers may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l, or a subset of these ingredients. In other embodiments the composition comprises two or more of the listed amino acids. The amino acid compositions work by correcting the cell shrinkage that occurs secondary to chloride secretions, and thus correct mucosal barrier defect and downstream local and systemic inflammation. The amino acid compositions correct dehydration in vascular, interstitial and intracellular compartment to restore the intracellular fluid volume and decrease the cell shrinkage and therefore paracellular permeability. The amino acid composition initially rehydrates the vascular and interstitial fluid compartments of the cells in the gut. Subsequently, the amino acid composition rapidly rehydrates the vascular, interstitital, and intracellular fluid compartments throughout the body. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity increase Villus height and crypt number.

In one embodiment a method for the promotion of increased Villus height and crypt number comprises administering to the subject, one of the compositions for the promotion of increased Villus height and crypt number described above.

Treatment of Environmental Enteropathy

In one embodiment, the compositions disclosed herein are used in a method for the treatment of environmental enteropathy symptoms.

A composition for the treatment of environmental enteropathy symptoms may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l, or a subset of these ingredients. In other embodiments the composition comprises two or more of the listed amino acids. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions work by correcting the cell shrinkage that occurs secondary to chloride secretions, and thus correct mucosal barrier defect and downstream local and systemic inflammation. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:

threonine at a concentration of between about 1 mg/L-10 mg/L,
tyrosine at a concentration of between about 1 mg/L-10 mg/L,
serine at a concentration of between about 1 mg/L-10 mg/L,
valine at a concentration of between about 1 mg/L-10 mg/L, and
tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L,
tyrosine at a concentration of between about 100 mg/L-5 gm/L,
serine at a concentration of between about 100 mg/L-5 gm/L,
valine at a concentration of between about 100 mg/L-5 gm/L, and
tryptophan at a concentration of between about 100 mg/L-5 gm/L.

In a most preferred embodiment the composition may comprise a combination of one or more of the following amino acids:

threonine at a concentration of between about 0.5 gm/L-2 gm/L,
tyrosine at a concentration of between about 0.5 gm/L-2 gm/L,
serine at a concentration of between about 0.5 gm/L-2 gm/L,
valine at a concentration of between about 0.5 gm/L-2 gm/L, and
tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity alleviates symptoms associated with environmental enteropathy.

In one embodiment a method for the treatment of environmental enteropathy symptoms comprises administering to the subject, one of the compositions for the treatment of environmental enteropathy symptoms described above.

Treatment of Weight Loss Caused by Cancer

In one embodiment, the compositions disclosed herein are used in a method for the treatment of weight loss caused by cancer.

A composition for the treatment of weight loss caused by cancer may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l;
and/or
serine at a concentration of about 420 to 3784 mg/l, or a subset of these ingredients. In other embodiments the composition comprises two or more of the listed amino acids. The amino acid compositions work by correcting the cell shrinkage that occurs secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity alleviates the symptom of weight loss caused by cancer.

In one embodiment a method for the treatment of weight loss caused by cancer comprises administering to the subject, one of the compositions for the treatment of weight loss caused by cancer described above.

Treatment of Norovirus Symptoms

In one embodiment, the compositions disclosed herein are used in a method for the treatment of norovirus symptoms such as diarrhea.

A composition for the treatment of norovirus symptoms may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l
tryptophan at a concentration of about 817 to 7352 mg/l;
asparagine at a concentration of about 528 to 4756 mg/l; and/or
serine at a concentration of about 420 to 3784 mg/l, or a subset of these ingredients. In other embodiments the composition comprises two or more of the listed amino acids. The amino acid compositions work by correcting the cell shrinkage that occurs secondary to chloride secretions, and thus correct muscosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:

threonine at a concentration of between about 1 mg/L-10 mg/L, tyrosine at a concentration of between about 1 mg/L-10 mg/L, serine at a concentration of between about 1 mg/L-10 mg/L, valine at a concentration of between about 1 mg/L-10 mg/L, and tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L, tyrosine at a concentration of between about 100 mg/L-5 gm/L, serine at a concentration of between about 100 mg/L-5 gm/L, valine at a concentration of between about 100 mg/L-5 gm/L, and tryptophan at a concentration of between about 100 mg/L-5 gm/L.

In a most preferred embodiment the composition may comprise a combination of one or more of the following amino acids:

threonine at a concentration of between about 0.5 gm/L-2 gm/L, tyrosine at a concentration of between about 0.5 gm/L-2 gm/L, serine at a concentration of between about 0.5 gm/L-2 gm/L, valine at a concentration of between about 0.5 gm/L-2 gm/L, and tryptophan at a concentration of between about 0.5 gm/L-2 gm/L.

The composition will not contain glucose or a carbohydrate that may be hydrolyzed into glucose in the gut.

Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity alleviates the symptom of noravirus infection.

In one embodiment a method for the treatment of the symptoms of norovirus infection comprises administering to the subject, one of the compositions for the treatment of norovirus infection symptoms described above.

Treatment of Food Poisoning Symptoms

In one embodiment, the compositions disclosed herein are used in a method for the treatment of the symptoms of food poisoning such as diarrhea.

A composition for the treatment of the symptoms of food poisoning may include one or more of the following constituents:

lysine at a concentration of about 730 to 6575 mg/l;
aspartic acid at a concentration of about 532 to 4792 mg/l;
glycine at a concentration of about 300 to 2703 mg/l;
isoleucine at a concentration of about 525 to 4722 mg/l;
threonine at a concentration of about 476 to 4288 mg/l;
tyrosine at a concentration of about 725 to 6523 mg/l;
valine at a concentration of about 469 to 4217 mg/l;
tryptophan at a concentration of about 817 to 7352 mg/l;
asparagine at a concentration of about 528 to 4756 mg/l; and/or
serine at a concentration of about 420 to 3784 mg/l, or a subset of these ingredients. In other embodiments the composition comprises two or more of the listed amino acids. The amino acid compositions work by correcting the cell shrinkage that occurs secondary to chloride secretions, and thus correct mucosal barrier defect and downstream local and systemic inflammation. The amino acid composition initially rehydrates the vascular and interstitial fluid compartments of the cells in the gut. Subsequently, the amino acid composition rapidly rehydrates the vascular, interstitial, and intracellular fluid compartments throughout the body. The amino acid compositions correct dehydration in vascular, interstitial and intracellular compartment to restore the intracellular fluid volume and decrease the cell shrinkage and therefore paracellular permeability. The composition does not contain glutamine, glucose or carbohydrates that can hydrolyze into glucose in the gut. The amino acids help move fluid into the three fluid compartments and therefore form a complete rehydration mechanism.

In another preferred embodiment, the composition may comprise a combination of one or more of the following amino acids:

threonine at a concentration of between about 1 mg/L-10 mg/L,
tyrosine at a concentration of between about 1 mg/L-10 mg/L,
serine at a concentration of between about 1 mg/L-10 mg/L,
valine at a concentration of between about 1 mg/L-10 mg/L, and
tryptophan at a concentration of between about 1 mg/L-10 mg/L.

In one embodiment the formulation may be formulated for parenteral administration such as intravenously.

In a more preferred embodiment the composition may comprise a combination of one or more of the following amino acids:

threonine at a concentration of between about 100 mg/L-5 gm/L,
tyrosine at a concentration of between about 100 mg/L-5 gm/L,
serine at a concentration of between about 100 mg/L-5 gm/L,
valine at a concentration of between about 100 mg/L-5 gm/L, and
tryptophan at a concentration of between about 100 mg/L-5 gm/L.

In a most preferred embodiment the composition may comprise a combination of one or more of the following amino acids:

threonine at a concentration of between about 0.5 gm/L-2 gm/L,
tyrosine at a concentration of between about 0.5 gm/L-2 gm/L,
serine at a concentration of between about 0.5 gm/L-2 gm/L,
valine at a concentration of between about 0.5 gm/L-2 gm/L, and
tryptophan at a concentration of between about 0.5 gm/L-2 gm/L.

The composition will not contain glucose or a carbohydrate that may be hydrolyzed into glucose in the gut. Glucose increases paracellular permeability (leaky gut). In addition glucose may further dehydrate the tissues.

The composition will also not contain glutamine, cysteine, methionine, and/or lactose.

The subject invention is based, at least in part, on the discovery that enteral feeding to subjects with only the nutrients that retain or acquire sufficient absorptive capacity alleviates the symptom of food poisoning.

In one embodiment a method for the treatment of the symptoms of food poisoning comprises administering to the subject, one of the compositions for the treatment of food poisoning symptoms described above.

Treatment of Wounds

The foregoing compositions may also be used as a topical application for wounds. The amino acid composition described above serves to reduce inflammation and enhance healing.

In one embodiment a method for the treatment of wounds comprises topically applying to the subject, one of the compositions described above.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A method for ameliorating symptoms of hangover in a subject in need thereof comprising:
   administering to the subject in need thereof, an effective amount of a formulation comprising free amino acids, wherein the free amino acids consist essentially of:
   free amino acids of aspartic acid, valine, serine, threonine, and tyrosine; and
   optionally electrolytes, vitamins, or minerals, or any combination thereof;
wherein the formulation does not comprise:
   free amino acid glutamine;
   a glutamine-containing dipeptide; or
   any combination thereof;
   or, when free amino acid glutamine, a glutamine-containing dipeptide, or any combination thereof is present, the free amino acid glutamine, the glutamine-containing dipeptide, or any combination thereof is present at a concentration less than 300 mg/l;
wherein the formulation does not comprise glucose;
   or, when glucose is present, glucose is present at a concentration of less than 1 g/l; and
wherein the formulation does not comprise:
   free amino acid methionine;
   a methionine-containing dipeptide; or
   any combination thereof;
   or, when free amino acid methionine, a methionine-containing dipeptide, or any combination thereof is present, the free amino acid methionine, the methionine-containing dipeptide, or any combination thereof is present at a concentration less than 300 mg/l; and
wherein the effective amount of the formulation is sufficient to ameliorate symptoms of hangover in the subject.

2. The method of claim 1, wherein the free amino acids consist of free amino acids of aspartic acid, valine, serine, threonine, and tyrosine.

3. The method of claim 1, wherein the formulation is formulated for oral administration.

4. The method of claim 1, wherein the formulation is administered through enteral feeding.

5. The method of claim 1, wherein the formulation is administered parenterally.

6. The method of claim 1, wherein the formulation is administered in pill form.

7. The method of claim 1, wherein aspartic acid is at a concentration of between 532 to 4792 mg/l, valine is at a concentration of between 469 to 4217 mg/l, serine is at a concentration of between 420 to 3784 mg/l, threonine is at a concentration of between 476 to 4288 mg/l, and tyrosine is at a concentration of between 725 to 6523 mg/l.

* * * * *